US00PP31206P2

(12) United States Plant Patent
Hansen

(10) Patent No.: US PP31,206 P2
(45) Date of Patent: Dec. 10, 2019

(54) ***LAGERSTROEMIA* PLANT NAMED 'BREW HA HA'**

(50) Latin Name: ***Lagerstroemia* (L.) hybrid**
Varietal Denomination: Brew Ha Ha

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 16/350,859

(22) Filed: Jan. 24, 2019

(51) Int. Cl.
*A01H 5/00* (2018.01)

(52) U.S. Cl.
USPC ..... Plt./252

(58) Field of Classification Search
USPC ..... Plt./252
CPC ..... A01H 5/00
See application file for complete search history.

*Primary Examiner* — Annette H Para

(57) ABSTRACT

The new and distinct crape myrtle plant named *Lagerstroemia* 'Brew Ha Ha' has a dense, short, compact, broadly-rounded habit, is ground hardy to at least USDA zone 6, has semi-glossy, deep bluish-green foliage blushed with dark purplish-red. The flowers arise from shiny, rosy-red buds, are lightly fragrant, large, cover the shrub with their vibrant bubblegum pink color. The new plant resists leaf spot and powdery mildew and is useful in the landscape as a specimen, en masse, or as a container plant.

1 Drawing Sheet

Botanical classification: *Lagerstroemia* (L.) hybrid.
Variety denomination: 'Brew Ha Ha'.

STATEMENT REGARDING PRIOR DISCLOSURES UNDER 37 CFR 1.77(b)(6)

The first public disclosure of the claimed plant, in the form of a photograph and brief description on a website operated by Walters Gardens, Inc. on Feb. 1, 2018. After that, on Mar. 12, 2018 the claimed plant was sold by Walters Gardens, Inc., who obtained the plant and all information relating thereto, from the inventor. No plants of *Lagerstroemia* 'Brew Ha Ha' have been sold in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to a new and distinct cultivar of *Lagerstroemia* plant, commonly known as Crape Myrtle, and hereinafter referred to by the cultivar name 'Brew Ha Ha' or the "new plant." 'Brew Ha Ha' is grown primarily as an ornamental for landscape use and for use as a potted plant and is the result of an ongoing breeding program to produce new and improved garden worthy plants for the ornamental market. The new plant was the result of pollination in an isolation block in August of 2012 at a wholesale perennial nursery in Zeeland, Mich., USA using the unreleased proprietary hybrid H10-11-22 (not patented) as the seed or female parent and the male or pollen parent is 'Cherry Mocha' U.S. Plant Pat. No. 28,281. The new plant was given the breeder code 12-27-9.

*Lagerstroemia* 'Brew Ha Ha' was initially asexually propagated by stem cuttings at a wholesale perennial nursery in Zeeland, Mich., USA in 2014. The resultant plants from successive generations have demonstrated that the new plant has remained stable and true to type in multiple and successive generations of asexual propagation.

SUMMARY OF THE INVENTION

Plants of the new cultivar 'Brew Ha Ha' have not been observed under all possible environmental conditions. The phenotype may vary somewhat with changes in light, temperature, soil and available moisture and fertility without, however, any variance in genotype.

The following traits have been repeatedly observed and are determined to be unique characteristics of 'Brew Ha Ha'. Among the characteristics in combination which distinguish 'Brew Ha Ha' as a new and distinct cultivar, unique from all other cultivars known to the inventor are:

1. Dense, short, compact, broadly-rounded growth habit;
2. Semi-glossy foliage of dark blue-green blushed with greyed-purple;
3. Heavily-branched reddish-brown colored stems;
4. Vibrant bubblegum-pink flowers open from rosy red buds on new growth to cover the shrub;
5. Resistance to *Cercospora* leaf spot and *Erisphe* powdery mildew;
6. Ground hardy to at least USDA hardiness zone 6.

The most similar cultivars known to the inventor include: 'Spiced Plum' U.S. Plant Pat. No. 29,478, 'Whit VI' U.S. Plant Pat. No. 14,438, 'Cool Beans' U.S. Plant Pat. No. 29,940, 'Sweet Macchiato' U.S. Plant Pat. No. 28,759, and the three copending cultivars 'Chaff Berry', 'Dark Roast' and 'Lava Java'. 'Spiced Plum' blooms about a week later with flowers that are more raspberry purple. 'Whit VI' is much larger in habit and has flowers of a different color. 'Cool Beans' has slightly larger habit and the flower color is a different pink hue. 'Sweet Macchiato' is slightly larger in habit and the flower color is more has lavender pink coloration. 'Chai Berry' is slightly taller in habit and the flower color is a different hue of rosy pink. 'Dark Roast' is slightly shorter in habit, the leaves are deeper reddish purple and the flowers are a different hue of bright fuchsia pink. 'Lava Java' is slightly taller in habit and the flowers are a deeper reddish hue. The female parent is slightly taller and more rounded in habit with denser branching and the flower color is more bubblegum pink with less lavender hue. The male parent, 'Cherry Mocha' is taller in habit, has darker burgundy foliage and the flowers are cherry red.

BRIEF DESCRIPTION OF THE DRAWINGS

The accompanying color photographs illustrate the flower and foliage characteristics and the overall appearance of a five-year-old plant of 'Brew Ha Ha', growing in a full-sun trial garden in Zeeland, Mich., showing the colors as true as it is reasonably possible to obtain in color reproductions of this type. Colors in the photographs may differ slightly from the color values cited in the detailed botanical description which accurately describe the colors of the new *Lagerstroemia*.

DETAILED BOTANICAL DESCRIPTION

Figure 1:
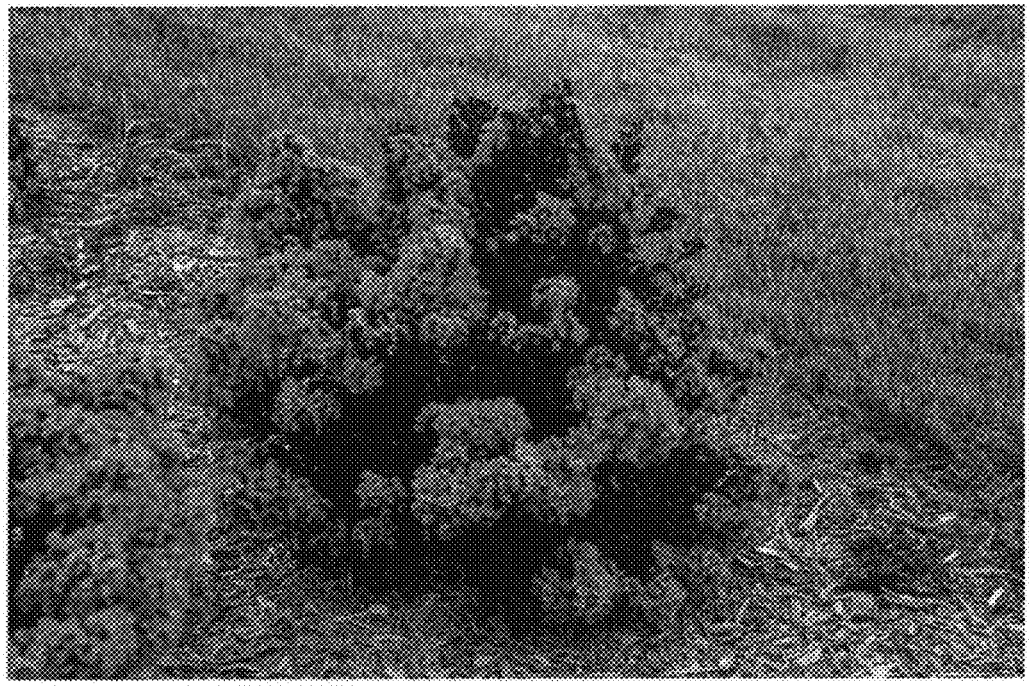
FIG. 1 shows a plant in a full-sun trial garden in late summer peak flowering.
Figure 2:
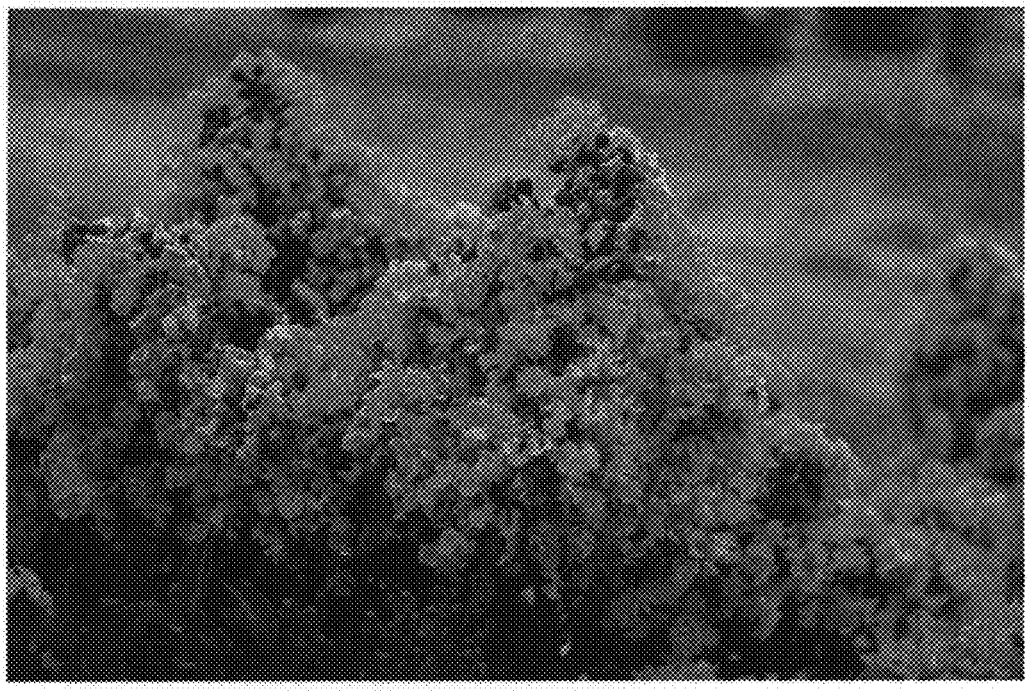
FIG. 2 shows a close-up for the flowers and buds.

The following color references are based on the 2015 edition of The Royal Horticultural Society Colour Chart except where common dictionary terms are used. The following observations and size descriptions are of approximately five-year-old plants grown in a loamy-sand, full-sun, open trial bed in Zeeland, Mich., USA with supplemental water and fertilizer as needed. The phenotype may vary slightly with different environmental conditions, such as temperature, light, fertility, moisture and maturity levels, but without any change in the genotype.

Botanical classification: *Lagerstroemia* L.;

Parentage: Female, or seed parent H10-11-22; the male, or pollen parent is 'Cherry Mocha';

Propagation: Terminal softwood stem cuttings;

Time to initiate roots: About three weeks;

Growth rate: Moderate; finishing from a 65 mm liner in a 3.7 liter container in about 10 to 14 weeks in the summer season;

Plant description: Deciduous, woody, narrow, compact flowering shrub; about six mainly upright to outward primary stems; freely branched;

Root description: Fine, numerous, fibrous, well-branched;

Plant habit: About 54.0 cm high from the soil level to the top of the inflorescences; about 68.0 cm wide with no pinching, pruning or plant growth regulators;

Stems: About six; to about 48.0 cm long and about 12.0 mm diameter at base; young stems cylindrical with four longitudinal carinae, along line on either side of petioles; basal stems cylindrical with slightly exfoliating bark; highly branched with about 12 to 20 alternate branches held at about 45 degree angle above horizontal; branches to about 25.0 cm long and 4.0 mm diameter at base;

Stem color: Woody basal portion variable with nearest RHS 177A and RHS 165C; young developing stems striated with nearest RHS 187B and nearest RHS 178C;

Node: About 20 to 25 per main stem; internode length average about 2.2 cm in main stems;

Node color: Same as surrounding stem;

Foliage description: Sub-opposite to alternate; simple; ovate; margin ciliolate, slightly involute; acute apex; aequilateral, rounded to attenuate base; to about 3.3 cm long and 2.0 cm wide, average about 2.9 cm long and 1.8 cm wide; adaxial and abaxial glabrous and lustrous;

Abaxial leaf color: Young emerging leaf adaxial between RHS 187A and RHS N186C, abaxial nearest RHS N186C; mature leaf adaxial nearest RHS NN137A with light blush of nearest RHS N187A, abaxial nearest RHS 138A lightly blushed with RHS N187A;

Veins: Pinnate, puberulent adaxial and abaxial;

Vein color: Young emerging adaxial between RHS 187A and RHS N186C, abaxial nearest RHS 186C; mature adaxial midrib nearest RHS 146C, secondary veins nearest RHS NN137A; mature abaxial midrib nearest RHS 160D with faint blush of nearest RHS 187C, secondary veins nearest RHS 160C with blush of nearest RHS N186C;

Petiole: Short, typically 1.0 mm long and 1.0 mm wide; color nearest RHS N187A both adaxial and abaxial of mature and young leaves;

Inflorescence: Panicle; terminal branched panicles up to about 600 flowers; average about 280 flowers; up to about 30.0 cm long and about 43.0 cm across; beginning late-summer and continuing until fall, for about six weeks;

Buds: Globose to ellipsoidal with rounded to slightly cuspidate apex and rounded base; lustrous; glabrous; about 8.0 mm long and about 7.0 mm diameter one day prior to opening;

Bud color: Exposed petals nearest RHS 64A; proximal one-half of calyx blend nearest RHS 187B, distal one-half of calyx nearest RHS 180B with carina nearest RHS 187B;

Flowers: Perfect; regular; actinomorphic; terminal panicle; individually about 2.5 cm across and about 24.0 mm long to tip of style, corolla to about 22.0 mm long; lasting about two days;

Flower fragrance: Faintly sweet;

Peduncle: Cylindrical with four longitudinal carinae in proximal portion and cylindrical in distal portion; about 5.0 mm diameter at base below lowest flowering branch, to about 30.0 cm long;

Peduncle color: Variable with position; proximal variable with nearest RHS 177A and RHS 165C and distal portion striated with nearest RHS 187B and nearest RHS 178C;

Pedicel: Cylindrical; glabrous; lustrous; about 6.0 mm long and 1.0 mm diameter;

Pedicel color: Nearest RHS 187A;

Sepals: Fused in about the basal 5.0 mm; acute apex, entire margin; glabrous and lustrous both adaxial and abaxial; about 8.0 mm long and individually and about 3.0 mm wide at fusion point;

Sepal color: Adaxial basal 3.0 mm nearest RHS 157D, middle 3.0 mm nearest RHS 187C, apical portion nearest RHS 157A with light blush nearest RHS N186C; abaxial nearest RHS 187B;

Petals: Six; stalked; glabrous; blade ruffled or crisped; margin crisped; blade with rounded apex and cordate to sagittate base, to about 15.0 mm across and 22.0 mm long; claw base or stalk adnate to calyx, to about 8.0 mm long and 0.5 mm diameter; overall about 22.0 mm long;

Petal color: Blade adaxial and abaxial nearest RHS 63A; claw nearest RHS 64B;

Androecium:

*Stamens*.—Typically about 42; six longer and about 36 shorter.

*Filaments*.—Shorter stamens to about 10.0 mm long and about 0.2 mm diameter, curved to twisted; longer filaments about 17.0 mm long and about 0.5 mm diameter; color of shorter filaments nearest RHS 50B; color longer filaments nearest RHS 50B.

*Anthers*.—Flattened ellipsoid; more developed on longer stamens to about 1.5 mm long and 1.2 mm across, on shorter stamens about 1.0 mm long and about 0.7 mm across; color nearest RHS 12C.

*Pollen*.—Abundant on longer stamens; color nearest RHS 13A.

Gynoecium: One; about 23.0 mm long;

*Style*.—Cylindrical; glabrous; about 20.0 mm long and 0.5 mm diameter; color nearest RHS 53A.

*Stigma*.—Globose; about 0.7 mm diameter; color nearest RHS 176B.

*Ovary*.—Superior; ellipsoidal; lustrous; about 3.0 mm tall and 2.0 mm diameter; color nearest RHS 154D.

Fruit: Globose; dehiscent, loculicidal, penta-valved capsule; 7.0 mm across and 9.0 mm long; immature color nearest RHS 146B, mature nearest RHS 199C;

Seed: Typically 12 to 24 per fruit; winged; to 6.5 mm long and 3.0 mm across and 1.0 mm thick at embryo; color between RHS 199D and RHS 161A;

Disease resistance: *Lagerstroemia* 'Brew Ha Ha' has shown resistance to powdery mildew and black leaf spot, *Erisphe* and *Cercospora* fungi, respectively. Other resistance beyond that typical for crape myrtle has not been observed. The new plant's root system is capable of withstanding cold temperatures typical of those found in USDA zone 6.

It is claimed:

1. A new and distinct cultivar of crape myrtle plant named 'Brew Ha Ha' essentially as herein illustrated and described.

* * * * *